Figure 1:
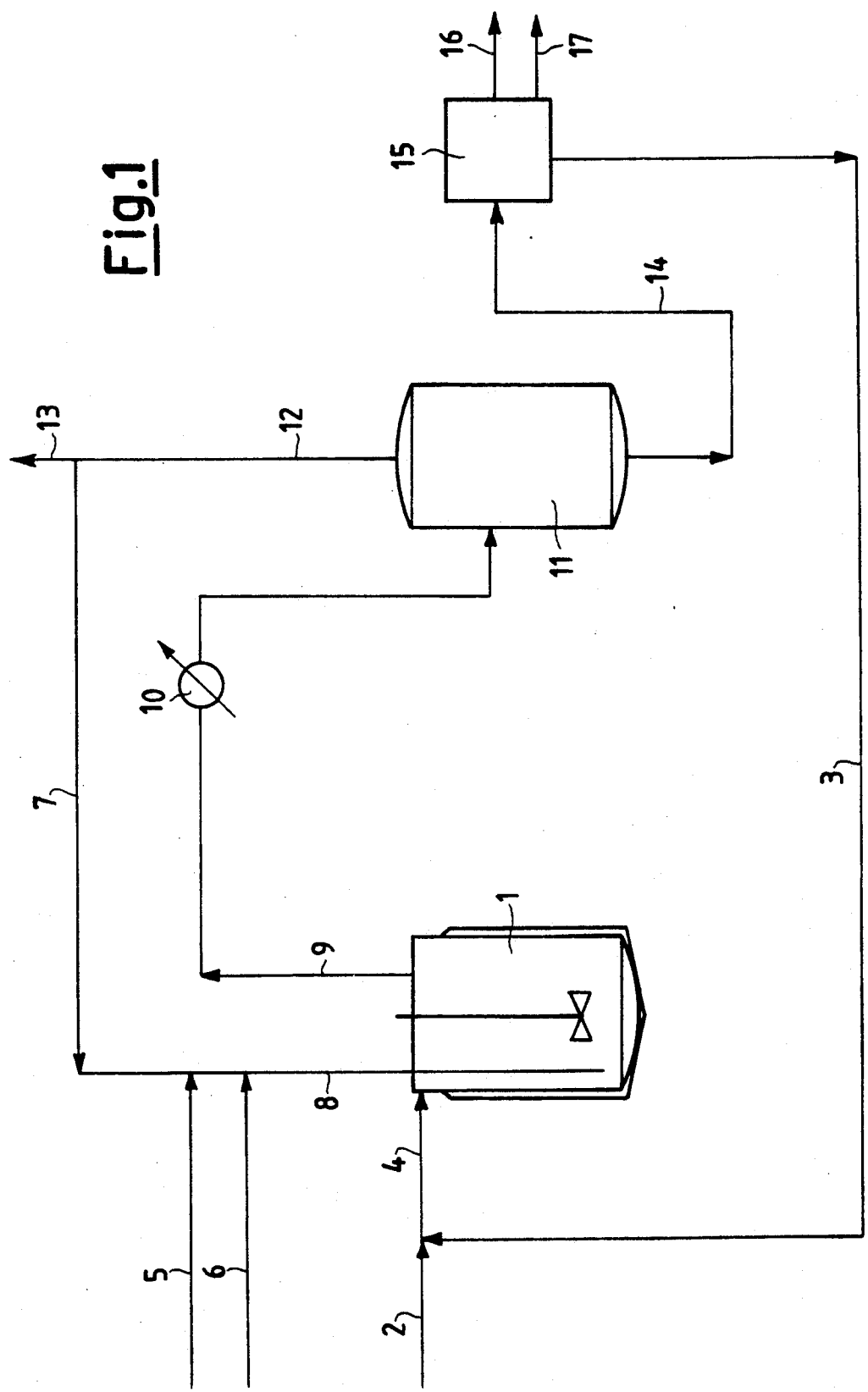

United States Patent [19]

Di Muzio et al.

[11] Patent Number: 5,210,269

[45] Date of Patent: May 11, 1993

[54] PROCESS FOR PRODUCING DIMETHYL CARBONATE

[75] Inventors: Nicola Di Muzio, Peschiera Borromeo; Carlo Fusi, Bergamo; Franco Rivetti, Milan; Giacomo Sasselli, San Donato Milanese, all of Italy

[73] Assignee: Enichem Synthesis S.p.A., Palermo, Italy

[21] Appl. No.: 709,583

[22] Filed: Jun. 3, 1991

[30] Foreign Application Priority Data

Jun. 4, 1990 [IT] Italy ................................ 20530 A/90

[51] Int. Cl.$^5$ ..................... C07C 68/00; C07C 69/96; B01J 27/122
[52] U.S. Cl. ..................................... 558/277; 558/260
[58] Field of Search .................................. 558/260, 277

[56] References Cited

U.S. PATENT DOCUMENTS 3,846,468 11/1974 Perrotti et al. ...................... 558/260
5,142,087 8/1992 Joerg et al. ......................... 558/277

Primary Examiner—Floyd D. Higel
Attorney, Agent, or Firm—Shea & Gould

[57] ABSTRACT

Dimethyl carbonate is prepared by means of a continuous process:
* by feeding, to a reaction chamber, methanol, carbon monoxide and oxygen, to a liquid reaction mixture with substantially constant composition and volume, containing methanol, dimethyl carbonate, water, and a copper catalyst;
* vaporizing from the reaction mixture a stream of methanol, water and dimethyl carbonate, which is developed together with the carbonmonoxide-containing gas stream; and
* recovering water and dimethyl carbonate from said vaporized mixture, in amounts substantially equal to the respective amounts thereof which are formed in the reaction chamber and recycling the other components.

The process, which is essentially characterized in that in the liquid reaction mixture a methanol concentration and a water concentration are maintained which are respectively equal to, or higher than, 30% by weight, and equal to, or lower than, 10% by weight, makes it possible dimethyl carbonate to be obtained with an improved productivity.

10 Claims, 1 Drawing Sheet

PROCESS FOR PRODUCING DIMETHYL CARBONATE

The present invention relates to a continuous process for producing dimethyl carbonate with high productivity values.

Dimethyl carbonate is an extremely versatile product which finds use as an organic solvent and additive for fuels, or a reactant, as a substitute for phosgene, in the synthesis of other alkyl or aryl carbonates useful as synthetic lubricants, solvents, plasticizers and monomers for organic glasses and in reactions of methylation and carbonylation for preparing isocyanates, urethanes and polycarbonates.

The usual route to prepare dimethyl carbonate consists in the reaction of methanol with phosgene, as described, e.g., in Kirk-Othmer, Encyclopedia of Chemical Technology, 3rd Edition, Volume 4, page 758. Such a process shows several disadvantages resulting from the use of phosgene and the co-production of hydrogen chloride, with consequent safety and corrosion problems, and the need for using a hydrogen chloride acceptor.

Therefore, alternative processes were developed in the past to replace the phosgene-based process; among these, the process based on the oxidative carbonylation of methanol in the presence of catalyst was particularly successful during the past years. The catalysts used for such a process of oxidative carbonylation are generally constituted by copper compounds, as disclosed, e.g., in U.S. Pat. Nos. 3,846,468; 4,218,391; 4,318,862; 4,360,477; 4,625,044; EP-A-71,286, EP-A-134,668; EP-A-217,651; DE-A-3,016,187 and DE-A-3,016,187.

EP-A-134,668 discloses a continuous catalytic process for producing dialkyl carbonates, in which an aliphatic alcohol, carbon monoxide and oxygen are fed to a liquid reaction mixture from which a stream containing the reaction products, dimethyl carbonate and water, is continuously evaporated. A critical aspect of the process of EP-A-134,668 consists in that at each time in the liquid reaction mixture a low level of alcohol (preferably less than 5% by weight) and a low water level (preferably less than 1% by weight) has to be maintained.

The low water content prevents catalyst deactivation phenomena from occurring and the low alcohol level makes it possible to easily remove the co-produced water—which is removed as an azeotropic mixture with dimethyl carbonate.

Unfortunately, it was observed that, by operating under the conditions of EP-A-134,668, the drawback occurs that the productivity to dialkyl carbonate is low, with the term "productivity" meaning the amount of dialkyl carbonate which is produced per unit useful reactor volume, and per time unit. This fact renders the same process not very attractive for an application on a commercial scale.

Therefore, the purpose of the present invention is a catalytic process for the continuous, high-productivity production of dimethyl carbonate, which overcomes the drawbacks of the prior art, as reported hereinabove.

In particular, the present Applicant has found, according to the present invention, that a high rate of conversion of the reactants, and a high selectivity to dimethyl carbonate can be attained if methanol, carbon monoxide and oxygen are fed to a liquid reaction mixture which contains a copper catalyst, in which liquid reaction mixture the concentration of methanol is maintained, at any time, at a level of at least 30% by weight. The present Applicant has found also that if one operates under these conditions, the concentration of water in the reaction mixture is not particularly critical, as regards the phenomena of catalyst deactivation, and that maintaining the water level always equal to, or less than, 10% by weight, is enough.

In accordance therewith, the present invention relates to a process for the continuous preparation of dimethyl carbonate, which process comprises:

(a) feeding methanol, carbon monoxide and oxygen to a reaction chamber which is maintained under reaction conditions and which contains a liquid reaction mixture consisting of methanol, dimethyl carbonate, water, and a copper catalyst;

(b) vaporizing from the reaction mixture a stream of methanol, water and dimethyl carbonate, which is developed together with the carbon-monoxide-containing gas stream; and (c) recovering from said vaporized mixture water and dimethyl carbonate in amounts substantially equal to the respective amounts thereof formed in the reaction chamber; and recycling the other components to the reaction chamber;

said process being essentially characterized in that the composition and the volume of the liquid reaction mixture are kept substantially constant over time, with methanol concentration and water concentration being respectively kept equal to, or higher than, 30% by weight, and equal to, or lower than, 10% by weight, relative to the weight of the same mixture.

More particularly, according to the present invention:

(a) a stream of both fresh and recycled methanol, carbon monoxide and oxygen and recycled dimethyl carbonate is fed, in a reaction chamber, to a liquid mixture with substantially constant composition and volume, containing methanol, dimethyl carbonate, water, and a copper catalyst, with methanol concentration and water concentration being constantly kept respectively equal to, or higher than, 30% by weight, and equal to, or lower than, 10% by weight;

(b) from the reaction methanol, an amount substantially equal to the amount of water formed in the reaction chamber of (a) and an amount of dimethyl carbonate greater than the amount of dimethyl carbonate formed in the reaction chamber in (a) are vaporized (together with the carbon-monoxide-containing gas stream); and (c) from the so vaporized stream:
  (i) a carbon-monoxide-containing gas stream,
  (ii) a first liquid stream consisting of water and dimethyl carbonate, in amounts substantially equal to the respective amounts thereof which are formed in the reaction chamber in (a);
  (iii) a second liquid stream consisting of methanol and of the excess of dimethyl carbonate over the amount of dimethyl carbonate formed in the reaction chamber in (a) are separated;

with the gas stream (i) and the liquid stream (iii) being recycled to the reaction chamber of (a) and the liquid stream (ii) being recovered.

The reaction of formation of dimethyl carbonate from methanol, carbon monoxide and oxygen takes place in the presence of a catalyst, in particular a copper catalyst. The catalyst is generally supplied as cuprous chloride which, in the reaction chamber and under the reaction conditions, can generate such species as copper methoxychloride and copper chlorohydroxides. Of course, the catalyst can also be directly fed to the reaction as copper methoxychloride and/or copper chlorohydroxides. Finally, active catalytic mixtures can be preformed by bringing into contact, outside of the reaction chamber, copper chlorides, oxides, hydroxides or carbonates.

According to the description published in I.E.C. Product and Research Development, Volume 19, pages 396-403, 1980, the catalytically active species can be represented by copper methoxychloride

[Cu(OMe)Cl]

formed in situ from oxygen, cuprous chloride (CuCl) and methanol, and that constitutes the basis for the establishment of a catalytic cycle in that the reaction of formation of dimethyl carbonate involves the reduction of Cu-(II) to Cu-(I), according to the following reaction scheme:

$2CuCl + 2MeOH + \frac{1}{2}O_2 \rightarrow 2Cu(OMe)CL + H_2O2$-
$Cu(OMe)Cl + CO \rightarrow 2CuCl + (MeO)_2CO$ Therefore, the global reaction leading to the formation of dimethyl carbonate from methanol, carbon monoxide and oxygen can be represented as follows:

$2MeOH + CO + \frac{1}{2}O_2 \rightarrow (MeO)_2CO + H_2O$

The critical aspect of the process of the present invention consists in limiting the conversion of methanol per each pass through (a), in such a way that the reaction is carried out in a liquid reaction mixture in which, at any time, the concentration of methanol and the concentration of water are respectively kept constantly equal to, or higher than, 30% by weight, and equal to, or lower than, 10% by weight. In particular, the concentration of methanol and of water in the reaction mixture can be respectively comprised within the range of from 30 to 80% by weight, and within the range of from 1 to 10% by weight.

In the preferred form of practical embodiment, the process is carried out with a liquid reaction mixture having a composition comprised within the following ranges of values:
* methanol from 35% to 70% by weight, and
* water from 2 to 7% by weight,
* with the balance to 100% being essentially constituted by dimethyl carbonate and unavoidable impurities.

Furthermore, the liquid reaction mixture will contain the copper catalyst in an amount comprised within the range of from 5 to 30 parts by weight, expressed as cuprous chloride, per each 100 parts by weight of the same mixture.

To the above disclosed reaction mixture both fresh and recycled methanol, carbon monoxide and oxygen are fed together with recycled dimethyl carbonate, with the amounts of the fresh reactants being equivalent to the amounts converted in the reaction chamber.

The reaction temperature in (a) can be generally comprised within the range of from 70° to 150° C. Temperatures higher than as indicated are not desirable, because they cause a decrease in reaction selectivity, with byproducts being formed at the expense of methanol, with the formation of carbon dioxide being increased and the catalyst being deactivated. Lower temperatures than as indicated are undesirable due to the low reaction kinetics. However, it is preferable to operate at temperatures close to the high limit of this range in order to have high reaction rates, as well as high values of vapour tension of water and of the organic constituents, with their removal from the reaction chamber being thus favoured. In practice, the preferred reaction temperatures are comprised within the range of from 120° to 140° C.

The pressures at which the reaction is carried out in (a) may vary within wide limits and will anyway be such as to maintain the reaction mixture in the liquid phase at the operating temperature. The preferred pressure values are comprised within the range of from 15 to 40 kg/cm$^2$, on considering that lower pressures than as indicated undesirably slow down the reaction kinetics, whilst higher values do not enable adequate concentrations of the organic components and water removed by the gas stream developing from the reaction mixture to be obtained.

To the liquid reaction mixture in (a) a gas stream containing carbon monoxide, oxygen and, optionally, inert gases, is fed, with the latter being contained at levels of up to 50% by volume in the gas mixture. By "inert gases", such gases as nitrogen, hydrogen or methane, which can be intentionally fed to the reaction chamber, and carbon dioxide, formed as a reaction byproduct, are understood. In the gas stream fed to (a), the molar ratio of carbon monoxide plus any possible inert gases, to oxygen, is kept comprised within the range of from 100:1 to 20:1.

By operating under the above conditions, from the liquid reaction mixture a stream of dimethyl carbonate, water and methanol, which is developed together with the excess of carbon monoxide, any possible unreacted oxygen, carbon dioxide and other possibly present inert gases, is removed in (b). Under these conditions, the catalyst, mostly present as a suspended solid, is not removed, and therefore the process can be carried out with high catalyst concentrations, with evident advantages from the viewpoint of the reaction rate.

By carrying out the removal of the reaction products by vapourization, owing to the liquid-vapour equilibria of methanol/dimethyl carbonate/water system, the amount of water removed, within the range of useful compositions, is resultingly lower—as expressed as mols —to the removed amount, as mols, of dimethyl carbonate. Inasmuch as during the course of the reaction one mol of water is formed per each mol of dimethyl carbonate, the removal of produced water is the limiting factor which controls reaching the steady-state operating conditions required to carry out the process in continuous fashion. Keeping this into due account, the process according to the present invention is carried out with a large excess of carbon monoxide, relatively to the required amount for the reaction and possibly also in the presence of inert gases, so as to maintain a relatively high flowrate of the gas stream fed to (a). In particular, considering the temperatures at which the reaction is carried out in (a), the vapour pressure of the organic components is of the order of from 5 to 10 kg/cm$^2$ and the concentration of water, in the condensate separated from the gas stream leaving the reaction chamber, is of the order of 2-3% by weight, the flowrate of the gas stream fed in (a) is advantageously maintained at a value of from 200 to 1000 liters, referring to standard temperature and pressure conditions (STP), per each liter of useful volume of the reactor, and per each hour. By "useful reactor volume", the volume of the liquid reaction mixture is meant.

The gas stream exiting the reaction chamber is suitably treated in (c) by cooling to temperatures equal or close to room temperature values, in order to separate the condensable organic products and water, from a gas stream [stream (ii)], containing the excess of carbon monoxide, any possibly unreacted oxygen, besides carbon dioxide byproduct, and possible inert substances. This stream is recycled, after a preliminary partial vent or treatment having the purpose of maintaining the concentration of carbon dioxide in the system at a substantially constant level.

The liquid phase condensed in (c) typically contains 45-70% by weight of methanol, 2-3% by weight of water and 25-50% by weight of dimethyl carbonate. This liquid phase can be typically treated by means of the normal distillation and de-mixing techniques to separate a stream of water and dimethyl carbonate [stream (ii)], in an amount substantially equal to the amount formed in the reaction in (a), which is recovered, and a stream consisting of the unreacted methanol and dimethyl carbonate in excess over to the amount formed during the reaction [stream (iii)], which is recycled to the reaction in (a). The stream (ii) is treated in order to separate dimethyl carbonate from water.

By operating according to the process of the present invention, dimethyl carbonate can be prepared with a high selectivity and a productivity generally higher than 40 and which, depending on the adopted conditions, may be as high as about 150 grams of dimethyl carbonate per liter of useful reactor volume and per hour.

FIG. 1 of the accompanying drawing schematically shows a suitable apparatus for practicing the process according to the present invention. More particularly, in said figure by the reference numeral (1) the reactor, equipped with stirring means and heat-exchange jacket, is indicated, to which the stream of fresh methanol, and a stream of recycled methanol and dimethyl carbonate are respectively sent via the lines (2) and (3), the streams (2) and (3) being combined and fed to the reactor (1) via the line (4). The stream of fresh carbon monoxide is fed by means of the line (5), the stream of fresh oxygen is fed by means of the line (6) and a recycle stream containing carbon monoxide is fed by means of the line (7). The streams (5), (6) and (7) are combined with one another and are fed to the reactor (1) via the line (8). The stream exiting the reactor via the line (9) is cooled in the heat exchanger (10), the condensed organic products and water are collected in the collector (ii) and the residual gases are recycled to the reactor (1) through the line (7), after a preliminary vent inside the line (13).

From the collector (11), the organic condensate is sent, through the line (14), to the separation section (15) in which a stream of dimethyl carbonate and water [line (16)] is recovered and is separated from a stream of pro- methanol and dimethyl carbonate in excess, which is recycled [line (3)].

EXAMPLE 1

The apparatus schematically shown in FIG. (1) is used, in which the reactor (1) is a reactor with an inner enamel coating, provided with stirring means and a temperature-control jacket inside which a diathermic oil is circulated, which reactor contains 3 liters of reaction liquid phase and 480 g of cuprous chloride (CuCl) catalyst, equivalent to a concentration of 160 g/liter. The reactor is pressurized at a relative pressure of 24 kg/cm², and is heated at 125° C.

Under steady-state conditions, the following streams are fed to the reactor:
97 g/hour of methanol [line (2)];
1,013 g/hour of a recycle stream [line (3)] containing 78.0% by weight of methanol and 22% by weight of dimethyl carbonate; the streams (2) and (3), combined with each other, are fed to the reactor (1) through the line (4);
310 STP liters/hour of a stream of carbon monoxide and nitrogen, containing 64.5% by volume of carbon monoxide [line (5)];
25 STP liters/hour of 98% pure oxygen, with the balance to 100% being mainly constituted by argon [line (6)];
1 500 STP liters/hour of a recycled stream [line (7)] containing carbon monoxide, carbon dioxide and nitrogen, with 55% by volume of carbon monoxide and 0.5% by volume of oxygen, the balance to 100% being constituted by nitrogen, carbon dioxide and argon; the streams (5), (6) and (7), combined with one another, are fed to the reactor (1) through the line (8).

Under steady-state conditions, the average composition of the liquid mixture inside the reactor (1) is as follows:

| methanol | 61.5% by weight, |
| dimethyl carbonate | 33.0% by weight and |
| water | 5.5% by weight. |

The gas stream leaving the reactor (1) through the line (9) is cooled down to approximately 20° C. in the heat exchanger (10) and in the collector (11) a mixture is separated at an average rate of 1,170 g/hour, which has the following composition:

| methanol | 67.5% by weight, |
| dimethyl carbonate | 30.1% by weight, |
| water | 2.2% by weight and |
| volatile byproducts | 0.2% by weight. |

The gases, after separation of the organic condensate in the collector (11), are recycled [line (7)], after a preliminary vent of 280 STP liters/hour [line (13)]. The condensate is transferred from the collector (11) to the separation unit (15) through the line (14).

In the separation unit (15), an average amount of 130 g/hour of dimethyl carbonate and of 26 g/hour of water is separated [line (16)], by fractional distillation and de-mixing, from a stream of unreacted methanol and excess dimethyl carbonate, which is recycled to the reactor (1) through the line (3).

From the above data, a conversion of methanol of 11.0% is determined, with a molar selectivity to dimethyl carbonate of 95%, based on methanol. The productivity is of 43 g of dimethyl carbonate per liter of useful volume and per hour.

EXAMPLE 2

The process is carried out as in Example 1, with the following streams being fed to the reactor:
Line (2): 150 g/hour of methanol;
Line (3): 1,155 g/hour of a mixture containing: 77.5% by weight of methanol and 22.5% by weight of dimethyl carbonate;
Line (5): 200 STP liter/hour of carbon monoxide at 100%
Line (6): 40 STP liters/hour of oxygen at 98%;

Line (7): 1,500 STP liters/hour of a mixture containing: 85% by volume of carbon monoxide and 0.5% by volume of oxygen, the balance to 100% being constituted by carbon dioxide and small amounts of argon.

Furthermore, in the reactor (1) the process is carried out at a temperature of 135° C., with the liquid reaction mixture having the following average

| methanol | 55.6% by weight, |
| dimethyl carbonate | 38.0% by weight, and |
| water | 6.4% by weight. |

Through the line (13) 150 STP liters/hour of gas are vented.

Under these conditions, from the line (14) an average amount of 1,400 g/hour is recovered of a mixture containing:

| methanol | 63.9% by weight, |
| dimethyl carbonate | 32.9% by weight, |
| water | 2.8% by weight and |
| byproducts | 0.4% by weight. |

Furthermore, from the line (16) an average amount of 200 g/hour of dimethyl carbonate and 40 g/hour of water is recovered.

The conversion of methanol is consequently of 14.3%, with a molar selectivity to dimethyl carbonate of 95%. The productivity is of 67 g of dimethyl carbonate per liter of useful reactor volume and per hour.

EXAMPLE 3

The apparatus schematically shown in FIG. (1) is used, in which the reactor (1) is a reactor with an inner enamel coating, provided with stirring means and temperature-control jacket inside which a diathermic oil is circulated, which reactor contains 10 liters of reaction liquid and 2,600 g of cuprous chloride (CuCl) catalyst, equivalent to a concentration of 260 g/liter. The reactor is pressurized at a relative pressure of 24 kg/cm$^2$, and is heated at 130° C.

Under steady-state conditions, the following streams are fed to the reactor:
* 990 g/hour of methanol [line (2)];
* 6,820 g/hour of a recycle stream [line (3)] containing 77% by weight of methanol and 23% by weight of dimethyl carbonate; the streams (2) and (3), combined with each other, are fed to the reactor (1) through the line (4);
* 800 STP liters/hour of a stream of pure carbon monoxide [line (5)];
* 240 STP liters/hour of 98% pure oxygen, with the balance to 100% being mainly constituted by argon and nitrogen [line (6)];
* 10,000 STP liters/hour of a recycle stream [line (7)] containing carbon monoxide, carbon dioxide and small concentrations of oxygen and inert gases (argon, nitrogen), with 82% by volume of carbon monoxide and 1.0% by volume of oxygen, the balance to 100% being constituted by nitrogen, carbon dioxide and argon; the streams (5), (6) and (7), combined with one another, are fed to the reactor (1) through the line (8).

Under steady-state conditions, the average composition of the liquid mixture inside the reactor (1) is as follows:

| methanol | 57.0% by weight, |
| dimethyl carbonate | 36.0% by weight and |
| water | 6.9% by weight. |

The gas stream leaving the reactor (1) through the line (9) is cooled down to approximately 20° C. in the heat exchanger (10) and in the collector (11) a mixture is separated at an average rate of 7,930 g/hour, having the following composition:

| methanol | 61.0% by weight, |
| dimethyl carbonate | 35.3% by weight, |
| water | 3.4% by weight and |
| volatile byproducts | 0.3% by weight. |

The gases, after separation of the organic condensate in the drum (11), are recycled [line (7)], after preliminarily venting 400 STP liters/hour [line (13)]. The condensate is transferred from the collector (11) to the separation unit (15) through the line (14).

In the separation unit (15), by fractional distillation and de-mixing, an average amount of 1,350 g/hour of dimethyl carbonate and of 270 g/hour of water is separated [line (16)] from a stream of unreacted methanol and excess dimethyl carbonate, which is recycled to the reactor (1) through the line (3).

From the above data, a conversion of methanol of 17.0% is determined, with a molar selectivity to dimethyl carbonate of 97%, based on methanol. The productivity is of 135 g of dimethyl carbonate per liter of useful volume and per hour.

We claim:

1. Process for the continuous preparation of dimethyl carbonate, which process comprises:
(a) feeding methanol, carbon monoxide and oxygen to a reaction chamber maintained under reaction conditions and containing a liquid reaction mixture consisting of methanol, dimethyl carbonate, water, and a copper catalyst;
(b) vapourising from the reaction mixture a stream of methanol, water and dimethyl carbonate, which is developed together with the carbon-monoxide-containing gas stream; and
(c) recovering from said vapourised mixture water and dimethyl carbonate in amounts substantially equal to the respective amounts thereof formed in the reaction chamber; and recycling the other components to the reaction chamber;

said process being essentially characterized in that the composition and the volume of the liquid reaction mixture are kept substantially constant over time, with methanol concentration and water concentration being respectively kept equal to, or higher than, 30% by weight, and equal to, or lower than, 10% by weight, relatively to the weight of the same mixture.

2. Process according to claim 1, characterized in that:
(a) a stream of both fresh and recycled methanol, carbon monoxide and oxygen and recycled dimethyl carbonate is fed, in a reaction chamber, to a liquid reaction mixture with substantially constant composition and volume, containing methanol, dimethyl carbonate, water, and a copper catalyst, with methanol concentration and water concentration being constantly kept respectively equal to, or higher than, 30% by weight, and equal to, or lower than, 10% by weight;

(b) from the reaction methanol, a water amount substantially equal to the amount of water formed in the reaction chamber of (a) and an amount of dimethyl carbonate larger than the amount of dimethyl carbonate formed in the reaction chamber in (a) are vapourised (together with the carbon-monoxide-containing gas stream); and
(c) from the so vapourised stream:
(i) a carbon-monoxide-containing gas stream,
(ii) a first liquid stream consisting of water and dimethyl carbonate, in amounts substantially equal to the respective amounts thereof which are formed in the reaction chamber in (a);
(iii) a second liquid stream consisting of methanol and of the excess of dimethyl carbonate over the amount of dimethyl carbonate formed in the reaction chamber in (a) are separated;
with the gas stream (i) and the liquid stream (iii) being recycled to the reaction chamber of (a) and the liquid stream (ii) being recovered.

3. Process according to claim 1, characterized in that during the reaction in (a) the process is carried out with a catalyst fed as cuprous chloride, copper methoxychloride, copper chlorohydroxide or as a mixture obtained by bringing into contact copper chlorides, oxides, hydroxides or carbonates, said catalyst being present in an amount of from 5 to 30 parts by weight, expressed as cuprous chloride, per each 100 parts by weight of liquid reaction mixture.

4. Process according to claim 1, characterized in that in the liquid reaction mixture in (a) the concentration of methanol is comprised within the range of from 30 to 80% by weight and the concentration of water is comprised within the range of from 1 to 10% by weight.

5. Process according to claim 4, characterized in that the process is carried out with a liquid reaction mixture in (a), having a composition comprised within the following ranges of values:
* methanol from 35% to 70% by weight, and
* water from 2 to 7% by weight,
* with the balance to 100% being essentially constituted by dimethyl carbonate.

6. Process according to claim 1, characterized in that the reaction temperature in (a) is comprised within the range of from 70° to 150° C. and.

7. Process according to claim 1, characterized in that the reaction in (a) is carried out at a pressure comprised within the range of from 15 to 40 kg/cm$^2$.

8. Process according to claim 1, characterized in that to the reaction in (a) a gas stream containing carbon monoxide, oxygen and, optionally, inert gases, is fed, with the latter being contained at a level of up to 50% by volume in the gas mixture, with a molar ratio of carbon monoxide plus any possible inert gases, to oxygen, comprised within the range of from 100:1 to 20:1.

9. Process according to claim 1, characterized in that the flowrate of the gas stream fed in (a) is comprised within the range of from 200 to 1000 liters, referred to standard temperature and pressure conditions, per each liter of useful volume of the reactor, and per each hour.

10. A process according to claim 6, wherein the reaction temperature in (a) is in the range of from 120° to 140° C.

* * * * *